(12) United States Patent
Carlin et al.

(10) Patent No.: US 7,242,832 B2
(45) Date of Patent: Jul. 10, 2007

(54) DEVICE FOR TISSUE CHARACTERIZATION

(75) Inventors: Donald B. Carlin, Pennington, NJ (US); Gerard A. Alphonse, Princeton, NJ (US)

(73) Assignee: Medeikon Corporation

( * ) Notice: Subject to any disclaimer, the term of this patent is extended or adjusted under 35 U.S.C. 154(b) by 41 days.

(21) Appl. No.: 11/191,097

(22) Filed: Jul. 27, 2005

(65) Prior Publication Data

US 2006/0024007 A1 Feb. 2, 2006

Related U.S. Application Data

(60) Provisional application No. 60/591,279, filed on Jul. 27, 2004.

(51) Int. Cl.
| | |
|---|---|
| G02B 6/06 | (2006.01) |
| G01B 9/02 | (2006.01) |
| A61B 6/00 | (2006.01) |
| A61B 19/00 | (2006.01) |

(52) U.S. Cl. .......................... 385/116; 385/88; 385/89; 385/117; 385/119; 385/118; 356/479; 600/477; 600/478; 128/898

(58) Field of Classification Search ................ 385/116, 385/117, 118, 119, 38, 88, 89, 92; 600/473, 600/476, 477, 478; 128/898, 665; 604/114, 604/95; 606/12, 7, 15, 17; 356/479
See application file for complete search history.

(56) References Cited

U.S. PATENT DOCUMENTS

| 4,445,892 A | 5/1984 | Hussein et al. ............. 604/101 |
|---|---|---|
| 4,913,142 A | 4/1990 | Kuttrell et al. ................ 606/7 |
| 4,967,745 A | 11/1990 | Hayes ..................... 128/303.1 |
| 5,106,387 A | 4/1992 | Kittrell et al. ................ 606/15 |
| 5,192,278 A | 3/1993 | Hayes ........................ 606/15 |
| 5,290,275 A * | 3/1994 | Kittrell et al. ................ 606/15 |
| 5,693,043 A * | 12/1997 | Kittrell et al. ................ 606/15 |
| 5,733,835 A | 3/1998 | Sinofsky et al. ............ 502/125 |
| 6,134,003 A | 10/2000 | Tearney et al. ............. 356/345 |
| 6,175,669 B1 | 1/2001 | Colston ....................... 385/12 |
| 6,351,678 B1 | 2/2002 | Borders ...................... 700/83 |
| 6,834,915 B2 | 5/2002 | Everett .................. 297/256.13 |
| 6,445,939 B1 | 9/2002 | Swanson ..................... 600/342 |
| 6,485,413 B1 | 11/2002 | Boppart et al. ............. 600/610 |
| 6,706,004 B2 | 3/2004 | Tearney ..................... 600/587 |
| 2001/0047137 A1* | 11/2001 | Moreno et al. ............. 600/475 |
| 2003/0004430 A1 | 1/2003 | Casscells et al. ........... 600/545 |
| 2003/0191398 A1* | 10/2003 | Motz et al. ................. 600/478 |
| 2006/0103850 A1* | 5/2006 | Alphonse et al. ........... 356/479 |

FOREIGN PATENT DOCUMENTS

| WO | WO 02/096484 A | 12/2002 | ............. 385/147 X |
|---|---|---|---|
| WO | WO 2005/000115 A | 1/2005 | ............. 385/147 X |
| WO | WO 2005/025412 A | 3/2005 | ............. 385/147 X |

OTHER PUBLICATIONS

Kiviniemi, et al.; "Coronary artery diameter can be assessed reliably with transthoracic echocardiography"; AJP-Heart 286: 1515-1520, 2004.

Virmani, et al.; "Pathology of thin-cap fibroatheroma: a type of vulnerable plaque" Journal of Interventional Cardiology, vol. 16, No. 3, 267, 2003.

* cited by examiner

*Primary Examiner*—Brian M. Healy
(74) *Attorney, Agent, or Firm*—Pepper Hamilton LLP

(57) ABSTRACT

A probe for use in characterizing tissue. The probe includes a plurality of optical fibers and an optical element. Each fiber includes a distal portion and a proximal portion. The fibers transmit light through the fiber to a surrounding area and collect light reflected back from the surrounding area. The optical element may be adjacent an outer periphery of the distal portion of the plurality of optical fibers. The optical element reduces an optical path length through blood.

25 Claims, 7 Drawing Sheets

DEVICE FOR TISSUE CHARACTERIZATION

CROSS-REFERENCE TO RELATED APPLICATION

This application claims the benefit of U.S. Provisional Patent Application No. 60/591,279, filed Jul. 27, 2004 which is hereby incorporated by reference in its entirety.

BACKGROUND

1. Field of the Invention

The invention relates generally to inspection instruments, and more particularly to a system and device for detecting and characterizing tissue and a method thereof.

2. Description of Related Art

Certain types of vulnerable plaques in a patient's vasculature are likely to rupture. These plaques, once ruptured, are extremely dangerous and can swiftly cause the patient's death. It is therefore desirable to detect the existence of such high-risk plaques so that they can be disposed of before they rupture.

High-risk plaques are believed to be characterized by large lipid pools hidden behind vascular walls. Because these lipid pools are covered by vascular walls, they cannot be seen by visible light. However, infrared light can penetrate short distances into the vascular wall and can therefore be used to detect such plaques, as well as other intravascular pathology.

A difficulty associated with intravascular use of infrared radiation is that blood absorbs and scatters such radiation. This results in a reduction in the signal-to-noise ratio. As a result, it is desirable to minimize the extent to which infrared radiation propagates through the blood.

Various techniques, however, exist or are being developed to detect plaque or lesions and malformations using probes inserted by, for example, a catheter and placed in proximity to anatomical features that are or might cause health problems. Examples include Low-Coherence Interferometry (LCI) for sensing tissue characteristics or its related imaging embodiment, Optical Coherence Tomography (OCT).

LCI is an optical technique that relies on "coherence gating" to provide precise axial positioning of an object in the direction of light propagation. By focusing the light in a sample, a transverse resolution may also be obtained (perpendicular to the optical beam), thus allowing for the collection of information from a finite volume for imaging or optical characterization purposes.

OCT is an imaging technique which allows high resolution observation and characterization of tissue microstructure imaging with resolution on the order of microns. This technique measures detailed changes within a few millimeters of a non-transparent tissue structure. One drawback of OCT imaging is the time to acquire a large number of data points necessary to obtain an image over a sufficient area.

An example of removing blood from a measurement site is to purge or flush the site with saline solution. This technique provides a short window of opportunity during which a measurement can be taken through the transparent saline solution. However, once the saline disperses, blood flows back into the measurement site and obscures the vascular wall.

Another approach to removing blood from a measurement site is to displace it with an inflated balloon catheter. However, if the balloon is not sufficiently inflated, considerable blood remains between the balloon and the vascular wall. If the balloon is so inflated that it makes contact with the vascular wall, blood flow is obstructed. This can lead to ischemia at points downstream from the balloon. In addition, the pressure of the balloon on the vascular wall can trigger a rupture of the plaque.

Accordingly there is a need for a device and method for sensing or characterizing arterial tissue and minimizing light attenuation in blood to improve a signal-to-noise ratio to achieve better results.

SUMMARY

An embodiment of the invention is a probe for use in characterizing tissue. The probe includes a plurality of optical fibers and an optical element. Each optical fiber includes a distal portion and a proximal portion. The optical fibers direct transmitted light through the optical fiber to a surrounding area and collect light reflected back from the surrounding area. The optical element may be adjacent a portion of an outer periphery of a distal portion of each optical fiber.

The probe may further include a transparent housing intermediate to the outer periphery of each optical fiber and the optical element. The plurality of optical fibers may be embedded in or mounted on an inner surface wall of the housing. The plurality of optical fibers may be non-rotating. The plurality of optical fibers may include a central optical fiber or may include a hollow or solid structure having the same diameter as the optical fibers. The optical element may be transparent and may be continuous. The optical element may have a thickness of about 50 µm to about 5 mm. The optical element may be solid or may include a balloon having clear fluid. The probe may be utilized in interferometry such as low-coherence interferometry or spectroscopy applications. The tissue may be a vascular wall. The probe may allow blood flow to be maintained around the optical element.

Another embodiment is directed to an optical head for use in characterizing tissue. The optical head includes an optical element, a first beam-shaping element and a second beam-shaping element. The optical element includes an inner surface and an outer surface. The first beam-shaping element may be adjacent the inner surface of the optical element and the second beam-shaping element may be adjacent the outer surface of the optical element. The optical element may be located adjacent a portion of an outer periphery of a distal portion of at least one optical fiber in a device.

The optical head may include a redirection element. The optical head may be transparent. The optical element may have a thickness of about 50 µm to about 5 mm. The optical head may be utilized in low-coherence interferometry or spectroscopy applications. The optical element may be continuous around the outer periphery of the at least one optical fiber in the device. The device may be a probe, guide wire or catheter.

Another embodiment is directed to a method for detecting vulnerable plaque. The method includes providing a device. The device includes a plurality of optical fibers and an optical element. Each optical fiber includes a distal portion and a proximal portion. The optical element may be located adjacent a portion of an outer periphery of a distal portion of each optical fiber. The device may then be inserted in a cavity. Next, transmitted light is directed through the device onto an inner wall of the cavity. The light reflected back may be collected from the inner wall of the cavity and the collected data then may be utilized to locate the vulnerable plaque.

The method may further include the step of utilizing interferomerty or spectroscopy. The plurality of optical fibers may be non-rotating. The plurality of optical fibers may include a central optical fiber or may include a hollow or solid structure having the same diameter as the optical fibers. The device may further include a transparent housing intermediate the outer periphery of the plurality of optical fibers and the optical element. The device may include a probe, guide wire or catheter. The optical element may be solid.

Another embodiment is directed to a system for use in characterizing tissue. The system may include a plurality of optical fibers, an optical element and a device. Each fiber includes a distal portion and a proximal portion and transmits light through the optical fiber to a surrounding area and collects light reflected back from the surrounding area. The optical element may be adjacent a portion of an outer periphery of the distal portion of each optical fiber. The plurality of optical fibers and the optical element may be located within the device.

The plurality of optical fibers may be non-rotating. The plurality of optical fibers may include a central optical fiber or may include a hollow or solid structure having the same diameter as the optical fibers. The optical element may be located adjacent an outer surface of the plurality of optical fibers. The system further includes at least one of a beam-shaping element and a redirection element. The optical element may have a thickness of about 50 µm to about 5 mm. The system may be utilized in low-coherence interferometry or spectroscopy applications. The system may allow blood flow to be maintained around the optical element.

BRIEF DESCRIPTION OF THE DRAWINGS

Aspects, features, benefits and advantages of the embodiments of the present invention will be apparent with regard to the following description, appended claims and accompanying drawings where:

DETAILED DESCRIPTION

Figure 1:
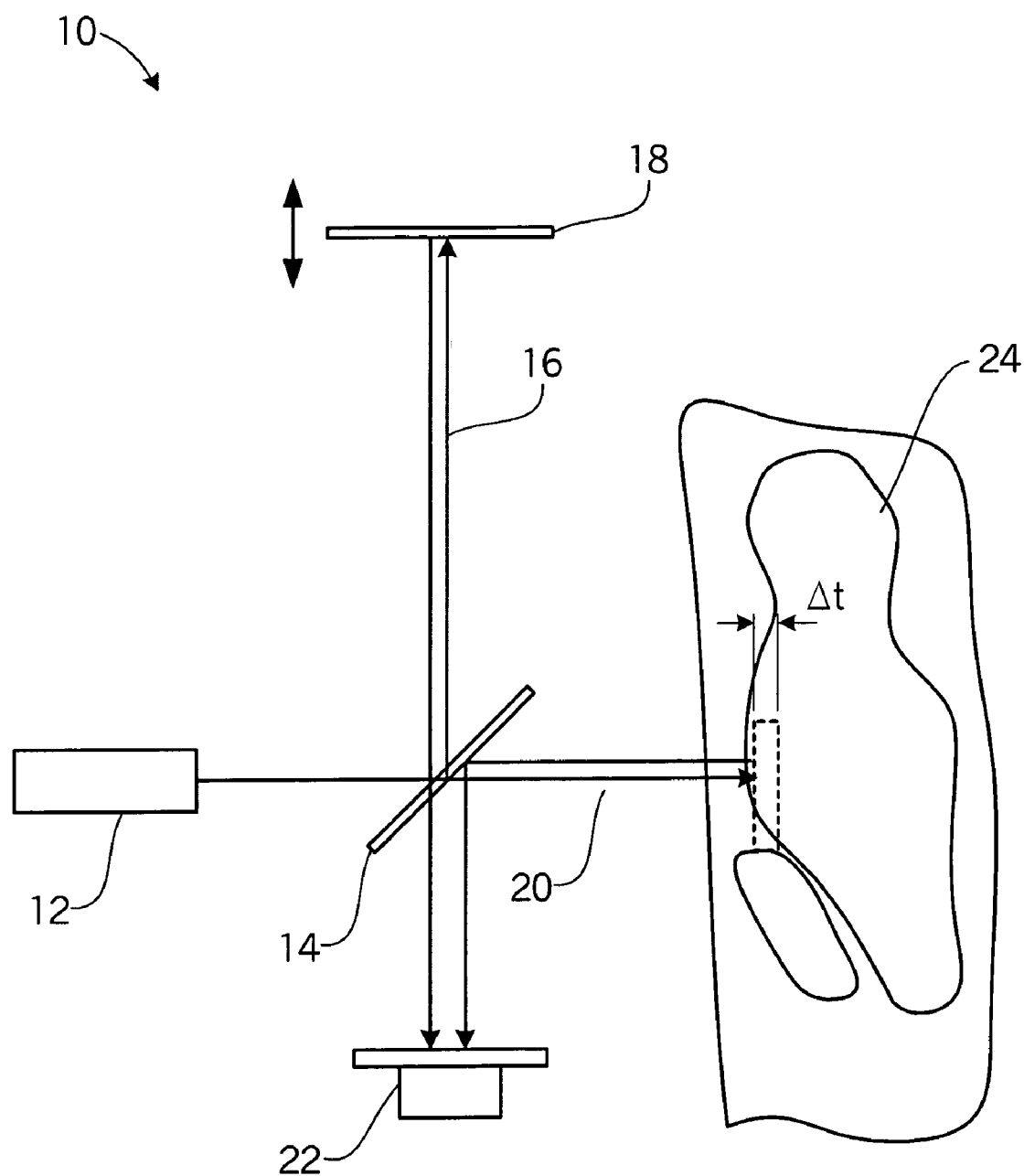
FIG. 1 is an illustration of LCI system probing a tissue sample.

The invention generally relates to a device and system that probes arterial tissue and a method of doing the same. In particular, the use of an optical element in a device over a portion of a light path reduces the optical path length through the blood, thereby increasing the signal-to-noise ratio. For example, FIG. 1 illustrates LCI, a system based on fiber optics, used to probe a tissue sample in blood. While FIG. 1 illustrates light in an interferometer propagating in free space, implementations based on fiber optics or waveguides may also be utilized. The LCI system 10 in FIG. 1 includes a broadband source light 12, a beamsplitter 14, a reference arm 16, a movable mirror 18, a sample arm 20, a detector system 22, and an object or tissue being examined 24. The beamsplitter 14 splits the source light 12 and directs it into two paths, a path that extends onto the tissue or object being measured along sample arm 20, and another path that reflects off the movable mirror 18 along reference arm 16.

The reference arm 16 provides a variable optical delay. Light input into reference arm 16 is reflected back by movable mirror 18 which translates in the horizontal and vertical direction. The reflected reference beam from reference arm 16 and a reflected sample beam from sample arm 20 pass back to the detector system 22, which processes the signals by techniques that are well known in the art to produce a backscatter profile (or "image") on display.

It is understood that the depth of sensing, $\Delta t$, the measurement of time in seconds, in a sample may be selected by positioning the movable mirror 18 of reference arm 16 such that the total optical paths of the sample arm 20 and reference arm 16 are equal. The signal directly backscattered from the sample 24 originates from a volume of depth, $\Delta t$, and a lateral extent equal to the dimension of a device of approximately up to 1 mm. The light source 12 may be a superluminescent diode, for example, which at an emission wavelength ($\lambda$) of about 1.3 µm may have a spread in wavelength of about 30 nm. The coherence length of such a source, as well as $\Delta t$, may be of the order of 20 µm.

With the use of any optical imaging system including the LCI system 10, a high signal-to-noise ratio is desirable so as to attain better detection and characterization results. A large factor in the limitation on the signal-to-noise ratio (S/N) commonly is the number of photons that are detected in a measurement interval. A lower number of photons results in a lower signal-to-noise ratio, and vice-versa. One manner in which a large number of photons per measurement may be achieved is to increase the time available per measurement sample which occurs when fewer data samples are obtained.

A signal-to-noise ratio can be calculated as follows. Given, an optical source with an optical power of 15 mW ex fiber and $\lambda=1.3$ µ, the rate at which photons are emitted, is of the order of $10^{17}$ per second. The number of photons, n, in a single sample measurement may then be calculated. This number may depend on a number of factors such as the originating photon flux, extinction in the blood due to scattering and absorption, the time allowed for each measurement, and geometrical factors, f, that encompass the fraction of emitted light that impinges on the probe area and the fraction of light scattered back towards the probe that is collected.

Additionally, a 2.5 ms/measurement time for each measurement can be obtained under the following assumptions: multiple fibers, each aimed at a specific portion of the circumference of the artery, an optical spot size of about 20 to 500 µm, 200 depth measurements made at each location, and $V_{axial}$, which represents the velocity at which the probe moves along the artery, of about 0.5 mm/s.

Figure 2:
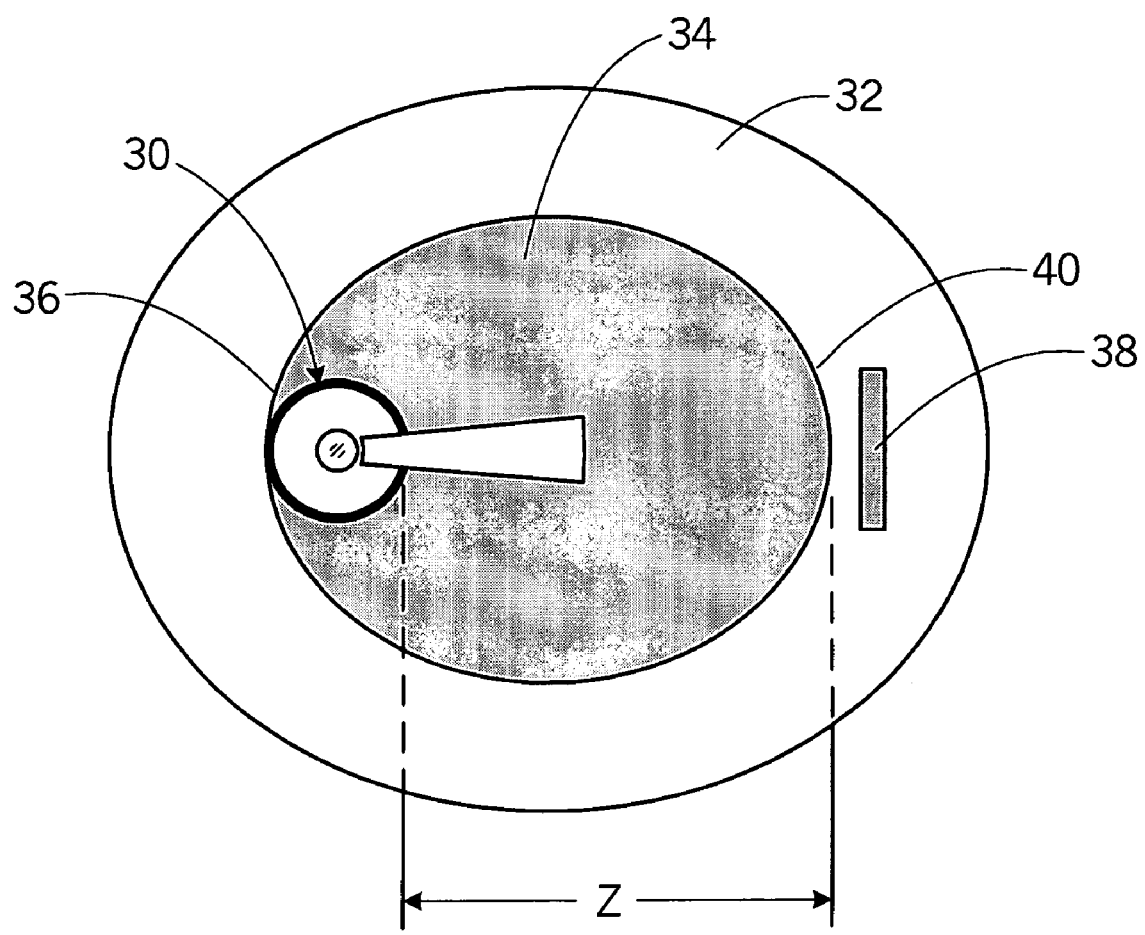
FIG. 2 is a top cross-sectional view of a small diameter probe in an artery sensing a tissue sample.

For example, FIG. 2 illustrates a cross-sectional view of a catheter 30 in an artery 32 having lumen 34. Catheter 30 is located on a side wall 36 of lumen 34 and illuminates a target 38 on or within an opposing side 40 or side wall of lumen 34. In operation, the light from catheter 30 must travel across the diameter of lumen 34 through the blood. This example considers a maximum optical path length through blood. Note that the depiction of circular symmetry of the lumen in FIG. 2 is reflective of a theoretical shape. The lumen of arteries in the body commonly depart from a circular symmetry, especially where lesions are present.

Assuming in this example that the diameter of lumen 34 is about 3 mm and catheter 30 is the same size as a guide, for example, about 0.3 mm, a direct optical path length through the blood, z, may be about 2.7 mm. The scattering and absorption of light at an absorption wavelength, $\lambda$, of about 1.3 mm are characterized by absorption coefficients: $\mu_s$ is about 2-3 mm$^{-1}$; $\mu_a$ is about 0.3-0.5 mm$^{-1}$. Optical extinction may be calculated by the following formula:

$$I(z)/I_0 = \exp[-(\mu_s + \mu_a)z] \quad (1)$$

Utilizing the maximum values described above, an extinction value of about $8 \times 10^{-5}$ is achieved. This extinction affects both rays of illuminating and return rays equally and is equal to about 82 dB of signal loss.

The number of photons/measurement, n, may be estimated by the following formula:

$$n = P_{in} \circ (\lambda/hc) \circ \Delta\tau \circ [(I(z)/I_0)^2] \circ f \quad (2)$$

where:

P$_{in}$ is the input power in Watt (typically 10 mW)
$\lambda$/hc is the number of photons in a Watt of optical power
$\lambda$ is about 1.3 µm
h=$6.626 \times 10^{-34}$ Joule-s
c=$2.998 \times 10^8$ m/s
$\lambda$/hc=$6.5 \times 10^{18}$ The value for $\Delta\tau$ is about 2.5 m/s and represents the time available for collection of photons. The fraction of incident light that is collected by the detection system is f. the detection system may include the same optical device that delivered the incident light. Experimental data indicates that f may be about $10^{-3}$ for simple probe systems. However, while f may vary from this estimate, this value will be utilized for the examples described herein.

In the above case, the number of photons passing through 2.7 mm of blood with a small diameter catheter can be calculated to be about $10^3$ photons as illustrated: n=($10^{-2}$ Joule/s)$\circ$($6.5 \times 10^{18}$)$\circ$($2.5 \times 10^{-3}$ s)$\circ$($6 \times 10^{-9}$)$\circ$($10^{-3}$). The number of photons yield a maximum S/N of 15 dB (due to shot noise). A 15 dB S/N ratio is considered to be relatively poor and may negatively effect the accuracy of sensing or detection. As can be seen in the calculations above, the largest contribution to the loss of photons is the 82 dB (the factor of $6 \times 10^{-9}$) loss due to extinction in the blood.

Figure 3:
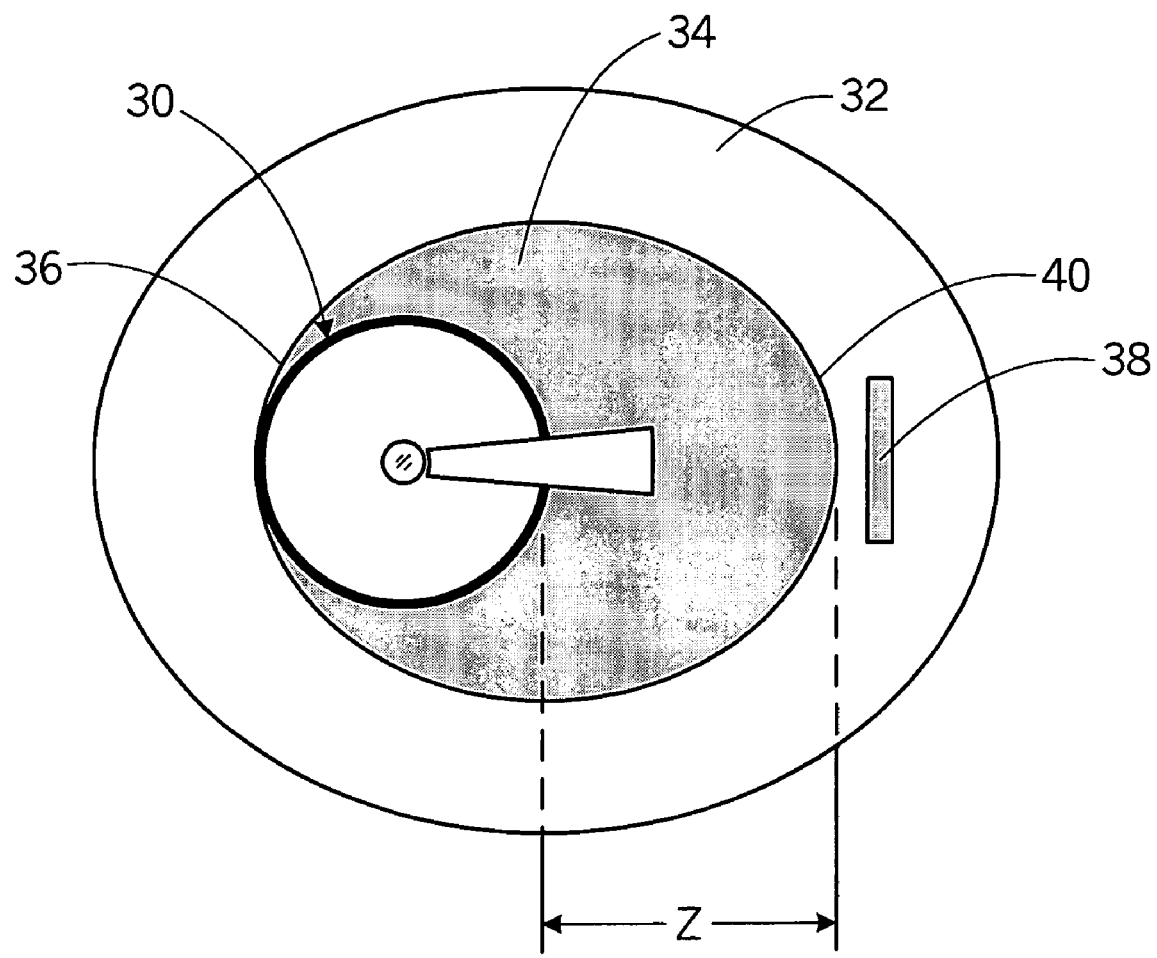
FIG. 3 is a top cross-sectional view of a larger diameter probe in an artery sensing a tissue sample.

FIG. 3 is a cross-sectional illustration of a catheter 30 of a larger size in artery 32. Catheter 30 is located on side wall 36 of cavity or lumen 34. The larger catheter 30 in FIG. 3 has a diameter of about 1.5 mm, which reduces the direct optical path through the blood, z, to about 1.5 mm. The single-pass extinction factor using formula (1) above is about $5 \times 10^{-3}$ or 23 dB ($2.5 \times 10^{-5}$) or 46 dB for two passes, (light going from the probe to the wall and then returning after scattering in the tissue). The number of photons, n, may be calculated utilizing formula (2) above and is calculated to be about $4 \times 10^6$ photons which yields about a 33 dB maximum S/N (due to shot noise). The use of a larger probe for the sensing of the tissue as demonstrated above yields a higher S/N ratio. Thus, in accordance with an embodiment of the invention, by decreasing the direct optical path through the blood, the attenuation of light in the blood may be reduced. This in turn, as shown with respect to FIG. 3, allows a greater number of photons to be detected, and accordingly which thereby improves the signal-to-noise ratio.

Figure 4:
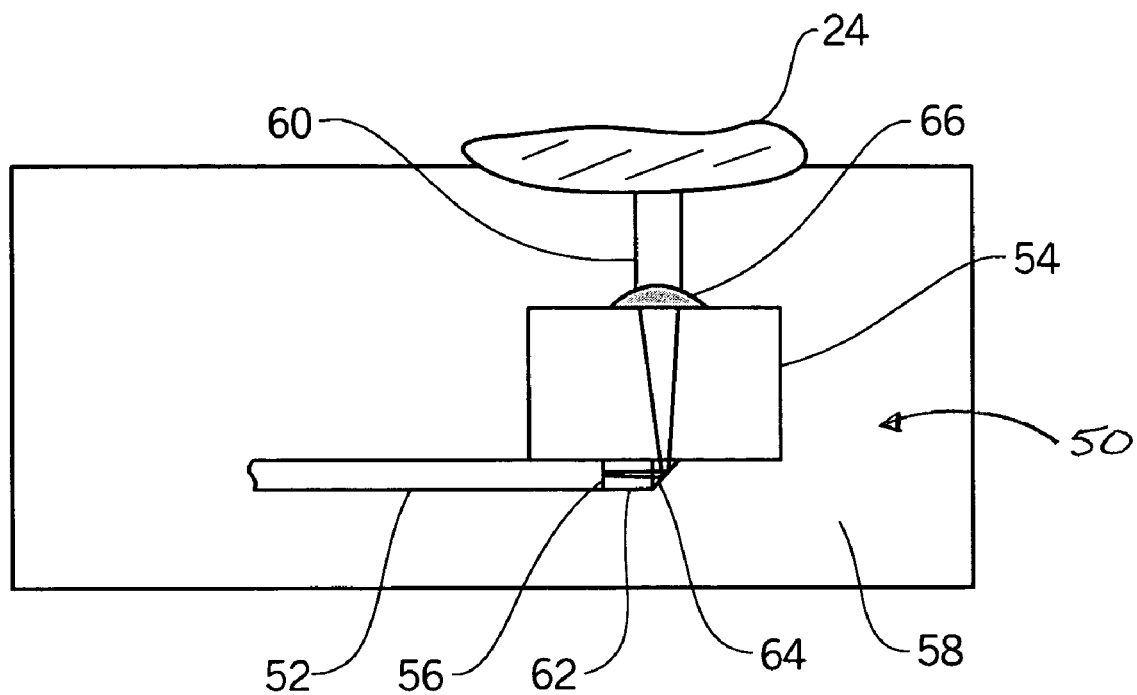
FIG. 4 is a schematic of a probe sensing a tissue sample.

FIG. 4 illustrates a device 50 in accordance with an embodiment of the invention. While the disclosure herein describes the device 50 as a probe, device 50 is not limited herein to a probe and may include other devices such as a guide wire, catheter, balloon, and the like. The probe 50 includes at least one optical fiber 52 and an optical element 54. The optical fiber 52 has a proximal end (not shown) and a distal end 56. The optical fiber 52 transmits and receives optical signals through a coupling fluid blood 58, for example, in a coronary artery. In particular, the optical fiber 52 detects light transmitted through the optical fiber 52 and through the blood 58, to a target area such as tissue being examined 24 and collects light reflected back from tissue 24.

Optical fibers 52 may be made of glass or a material and the like. Optical fibers 52 may be single mode or multiple mode optical fibers. Single mode fibers may be preferable for maximizing the longitudinal resolution. However, multimode fibers may be made smaller, thus maximizing radial resolution and device flexibility. Average sizes for single mode fibers may be on the order of about 100 µm diameter, while an average catheter diameter may be about 1 to 3 mm. Thus, a maximum of about 30 to 100 single mode fibers could be used. In a preferred embodiment, 1-12 optical fibers are utilized, more preferably 1-6.

As discussed above, a ruptured plaque causes sudden cardiac death (SCD) by interposing necrotic core material in sufficient volume to substantially occlude the artery. Pathological studies have shown a high-correlation between the area extent of the necrotic core or lipid pool, as a percentage of the total luminal area in that region. Additionally, only those necrotic cores with an angular extent of 120° or so would lead to SCD. Therefore, in an embodiment, three equally spaced optical fibers may be sufficient to detect vulnerable plaques. Additionally, utilizing more optical fibers reduces the possibility of not detecting the lesions. Accordingly, an embodiment includes at least 2, more likely at least 3, and more likely at least 6 optical fibers to detect critical lesions.

Figure 5A:
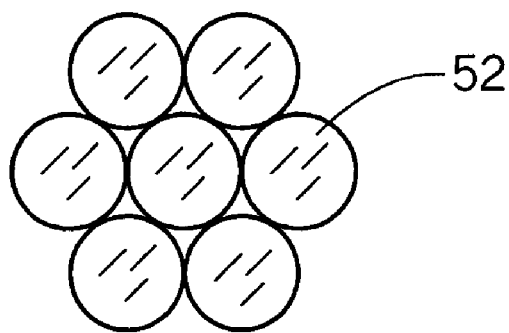
FIG. 5a is an arrangement of a plurality of optical fibers in an embodiment of the invention.
Figure 5B:
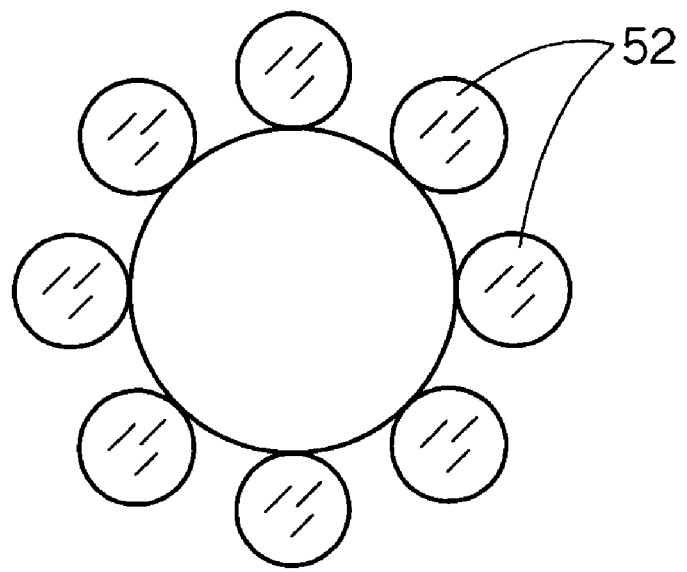
FIG. 5b is an arrangement of a plurality of optical fibers in another embodiment of the invention.

FIGS. 5a and 5b illustrate embodiments of optical fibers 52 in various arrangements. FIG. 5a illustrates an arrangement of seven optical fibers 52, all having the same diameter, in a device (not shown). The seven optical figures may be arranged adjacent each other and form a ring-like shape with a central area or opening. Alternatively, as shown in FIG. 5a, the six optical fibers may be arranged around an outer circumference of a seventh central optical fiber 53, with the seventh central optical fiber 53 having the same diameter as the other six optical fibers 52. Other arrangements include a hexagonal close packing arrangement, or other geometrical arrangements. While as illustrated, six optical fibers are adjacent to each other, the arrangement of the optical fibers is not limited to such, but may include optical fibers to be spaced at intervals around central optical fiber 53 as illustrated in FIG. 5b. FIG. 5b illustrates central optical fiber 53 of a large diameter surrounded by six optical fibers 52 each having a same smaller diameter than optical fiber 53 and surrounding the outer circumference of optical fiber 53. In other embodiments, the six optical fibers 52 may be of the same diameter, or optionally may vary from each other in diameter size. The arrangement of the plurality of fibers may vary and may depend on fabrication processes of the probe.

In another embodiment, central optical fiber 53 may be a structure. The structure may be hollow or may be a solid material. In embodiments where the structure is hollow, a central area opening may be defined by an inner periphery of the plurality of optical fibers. The central area opening allow blood flow to continue through the central opening within the plurality of optical fibers.

In another embodiment, optical fibers may be obtained with a cladding diameter of about 80-125 µm. For example, six optical fibers of 80 µm size may fit within a tube of the same diameter of a standard cardiac guide wire, of about 350 µm diameter and therefore may allow the optical probe to function as a guide wire. As described above, the use of multiple fibers in a probe is beneficial as it increases the circumferential coverage of the artery. In an alternate embodiment a separate detector or interferometer may be attached to each probe, that improves the dwell time and therefore the speed or signal-to-noise ratio.

The device 50 further includes optical element 54. Optical element 54 reduces the optical path length 60 through the blood 54 and is located adjacent the distal portion 56 optical fiber 52. In particular, optical element 54 reduces extinction of the light traveling from the emitting portion of the device to the target and from the target. Optical element 54 may have a thickness of about 50 µm-5 mm, preferably about 100 µm-4 mm. Optical element 54 may be uniform in thickness. In an alternate embodiment, the thickness of optical element 54 may vary. For example, one side of optical element 54 may be of a desired thickness and the opposing side may be thickness larger than the desired thickness.

The optical element 54 may be a solid material made of glass, plastic or other transparent material and the like. The shape of optical element 54 may vary. For example, optical element 54 may be a circular shape, a hexagonal shape, or a shape that corresponds to optical fibers 52. In an embodiment, one side of optical element 54 may be flat to allow the probe to be easily move in and or along a vascular wall, while the opposing side may be bevel shaped of a larger thickness to displace a larger amount of blood. In an alternate embodiment, a balloon, which may or may not have a variable width may be used as optical element 54. The balloon may be filled with clear fluid such as liquid or gas.

Figure 6A:
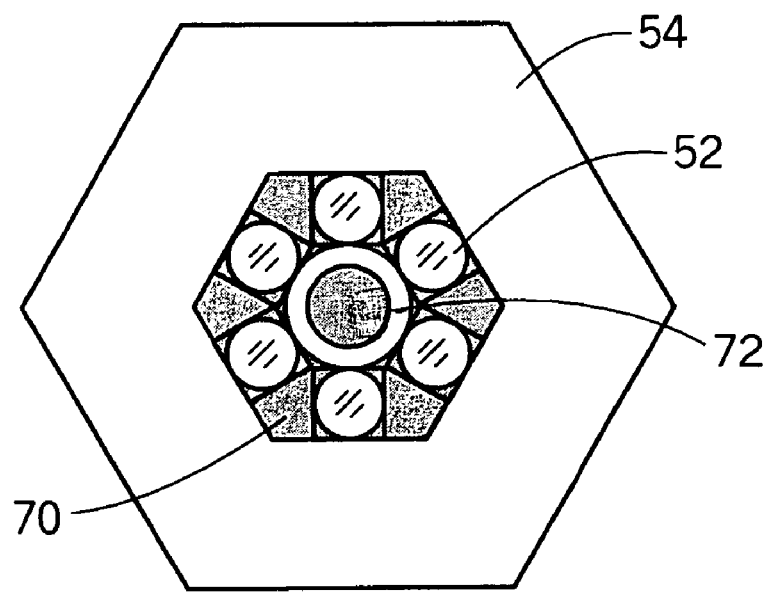
FIG. 6a is a probe with an optical element in accordance with an embodiment of the invention.

Optical element 54 may be located adjacent the distal end or portion 56 of optical fiber 52 along an outer periphery of optical fiber 52. Optical element 54 may be a continuous structure in contact with the outer periphery of optical fibers 52 as illustrated in FIG. 6a. Alternatively, optical element 54 may be non-continuous and located adjacent portions of optical fibers 52.

Figure 6B:
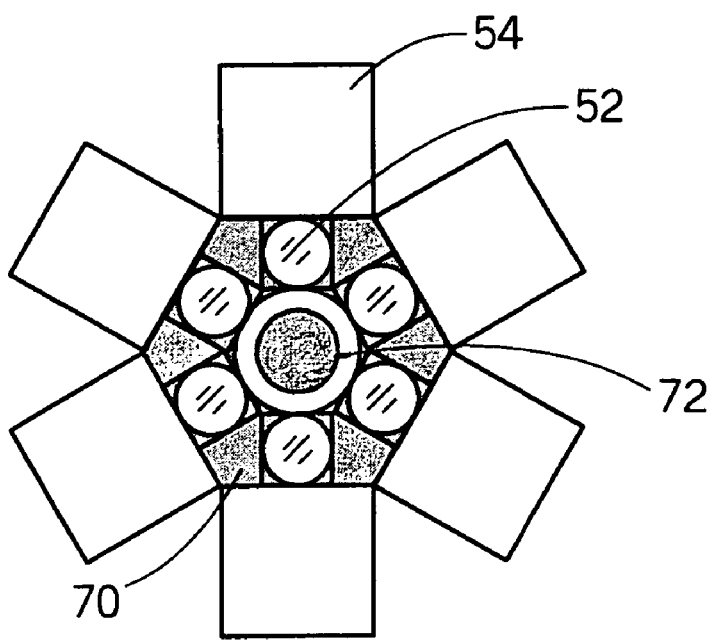
FIG. 6b is a probe with an optical element in accordance with another embodiment of the invention.

FIGS. 6a and 6b also illustrate another embodiment where a plurality of optical fibers may be bundled together to provide structural support within the device. Alternatively, the plurality of optical fibers may be located in a housing 70, such as a plastic cover, catheter wall or the like. As illustrated, the optical fibers may be located adjacent an internal surface of the housing 70. Optic fibers 52 are located at intervals centrally around the inner circumference of housing 70. Optical element 54 is continuous and located around the housing 70. Optical element 54 may be any shape including circular or may also a similar shape to that of the plurality of optic fibers 52 or housing 70. Located centrally within the plurality of optic fibers 52 is area 72.

In an alternate embodiment illustrated in FIG. 6b, optical element 54 may be non-continuous and independent and may be located adjacent optical fiber 54 via housing 70. Alternatively, the optical fibers may be embedded completely or partially, in the internal surface of the housing 70. The number of optical fibers around the circumference of the housing may be dependent on factors such as the limit of the device size, the fiber optic diameter, the desired speed of acquisition, and the necessary radial resolution.

As further illustrated in FIG. 4, the device 50 may optionally include additional elements. For example, device 50 may include a redirection element 62 and at least one beam-shaping element 64 and a second beam-shaping element 66. One beam-shaping elements 64, 66 and optical element 54 may be referred to as an optical head. The optical head may also include additional miniature optics as known in the art. Redirection element 62 may be a prism, a GRIN lens or the like. Redirection element may be located adjacent distal portion 56 of optical fiber 52. First, beam-shaping element 64 may be located adjacent redirection element 62. Redirection element 62 and first beam-shaping element 64 may be used for collimating and directing the light emerging from optical fiber 52 onto the lumen. Redirection element 62 and first beam-shaping element 64 may extend through a housing 70, as described below, or optically may be optically transparent to allow light to be transmitted to and received from the target. Second beam-shaping element 66 may be located adjacent a surface of optical element 54 opposite the surface of optical element 54 adjacent optical fiber 52. In alternate embodiments, different combinations of optical elements, for example, redirection element without beam-shaping element, beam-shaping element without redirection element, in addition to other combinations also including additional beam-shaping elements may be used. In alternate embodiments, redirection element 62 and beam-shaping element 66 may be coated to minimize unwanted reflections at the interface between the optical element 54 and blood 58.

In further detail as illustrated in FIG. 4, optical fiber 52 delivers light to and from optional beam-shaping element 64. The light may be redirected, for example, reflected, refracted or diffracted, by redirection element 62. The light is transmitted through optical element 54. To reduce or shorten the optical path length 60, the light must pass through the blood 28 to the tissue being examined 24. Additional, beam-shaping elements may be utilized. Both the light emitted from the system 10 and that collected by the system 10 are shown. For systems that use scattered light or emitted light such as interferometry or spectroscopy, light emanates in many different directions (not shown) from the tissue being irradiated. For optical probe systems using single-mode fibers, however, the light that is accepted for return, detection, and analysis by whatever system is attached to the end of the fiber (not shown) will have enter within the same angular and real constraints as are characteristic of the irradiating, emitted beam.

Figure 7:
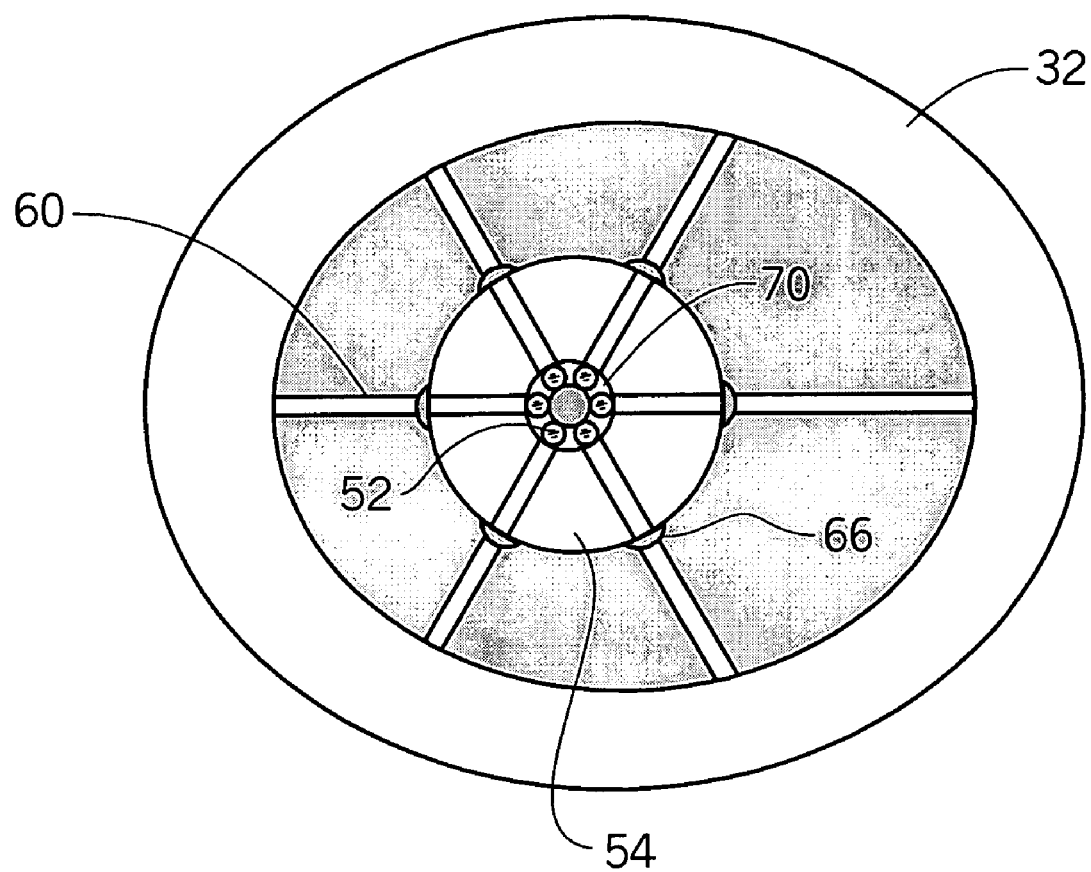
FIG. 7 is a device in accordance with an embodiment of the invention.

FIG. 7 illustrates another embodiment of the invention with probe 50 generally located centrally within artery 32. In other embodiments, probe 50 may be located along one side of an artery wall instead of centrally within the artery. The probe 50 may be located in any desired position to allow characterization of the tissue. In an embodiment the probe may be moved, for example, rocked to characterize or sense an entire area. This movement may provide a more comprehensive results in characterizing the tissue. In FIG. 7, probe 50 includes six optical fibers 52 located within housing 70. The optical fibers 52 are located at intervals along an inner circumference of the housing 70. Continuously surrounding the outer circumference of housing 70 is optical element 54. Beam-shaping element 66 is located on an outer surface adjacent to optical element 54 corresponding to each optical fiber 52. In other embodiments, the number of optical fibers 52 may vary.

Another embodiment is directed to an optical head for use in characterizing tissue. The optical head includes an optical element, a first beam-shaping element and a second beam-shaping element. The optical element includes an inner surface and an outer surface. The first beam-shaping element may be adjacent the inner surface of the optical element and the second beam-shaping element may be adjacent the outer surface of the optical element. The optical element may be located adjacent a portion of an outer periphery of a distal portion of at least one optical fiber in a device.

Another embodiment is directed to a method for detecting vulnerable plaque. The method includes providing a device. The device includes a plurality of optical fibers and an optical element. Each optical fiber includes a distal portion and a proximal portion. The optical element may be located adjacent a portion of an outer periphery of a distal portion of each optical fiber. The device may then be inserted in a cavity. Next, transmitted light is directed through the device onto an inner wall of the cavity. The light reflected back may be collected from the inner wall of the cavity and the collected data utilized to locate the vulnerable plaque.

The method may further include the step of utilizing low coherence interfiomerty or spectroscopy.

In alternate embodiments the probe described herein may be incorporated into balloons or other devices such as catheters, guide wires, and the like that measure location, thickness or structure of intra-cavity regions such as arterial walls. In other embodiments, the probe may be utilized as a guidance system. An addition to medical applications, the invention can be used for non-medical instruments which may be used to inspect and probe in situ locations.

Embodiments of the present invention may provide numerous advantages. For example, a high signal-to-noise ratio can be achieved by reducing the optical path length passing through blood. Additionally, the invention reduces the risk of injury to an inner wall of a blood vessel that can result from contact with the probe or device.

While the present invention is satisfied by embodiments in many different forms, there is shown in the drawing and described herein in detail, the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing form the scope and spirit of the invention. The scope of the invention will be measured by the appended claims and their equivalents.

What is claimed is:

1. A probe for use in characterizing tissue, comprising:
   at least one reference arm; and
   at least one sample arm comprising:
      plurality of optical fibers, each optical fiber having a distal portion and a proximal portion, the optical fibers directing transmitted light through the optical fiber to a surrounding area and collecting light reflected back from the surrounding area; and
      an optical element adjacent a portion of an outer periphery of a distal portion of each optical fiber.

2. The probe according to claim 1, wherein the plurality of optical fibers are non-rotating.

3. The probe according to claim 1, the probe further comprising a transparent housing intermediate the outer periphery of each optical filer and the optical element.

4. The probe according to claim 1, wherein the optical fibers are embedded in or mounted on an inner surface wall of the housing.

5. The probe according to claim 1, wherein the plurality of fibers may include a central structure.

6. The probe according to claim 1, wherein the optical element is transparent.

7. The probe according to claim 1, where in the optical element has a thickness of about 50 μm to about 5 mm.

8. The probe according to claim 1, wherein the optical element is solid.

9. The probe according to claim 1, wherein the optical element comprises a balloon having clear fluid.

10. The probe according to claim 1, wherein the probe is utilized in interferometry or spectroscopy applications.

11. The probe according to claim 1, wherein the optical element is continuous.

12. The probe according to claim 1, wherein the tissue is a vascular wall.

13. An optical head for use in characterizing tissue comprising:
   an optical element having an inner surface and an outer surface;
   a first beam-shaping element, wherein the first beam-shaping element is adjacent the inner surface of the optical element; and
   a second beam-shaping element, wherein the second beam-shaping element is adjacent the outer surface of the optical element,
   wherein the optical element is located adjacent a portion of an outer periphery of a distal portion of at least one optical fiber in a device having at least one reference arm and at least one sample arm.

14. The optical head according to claim 13, wherein the optical head is transparent.

15. The optical head according to claim 13, wherein the optical element has a thickness of about 50 μm to about 5 mm.

16. The optical head according to claim 13, further comprising a redirection element.

17. The optical heard according to claim 13, wherein the optical head is utilized in interferometry or spectroscopy applications.

18. The optical head according to claim 13, wherein the optical element is continuous around the outer periphery of the at least one optical fiber in the device.

19. The optical head according to claim 13, wherein the device comprises one of a probe, guide wire or catheter.

20. A method for detecting vulnerable plaque, comprising:
   providing a device having at least one reference arm and at least one sample arm, said sample arm comprising a plurality of optical fibers, each optical fiber having a distal portion and a proximal portion, and an optical element, wherein the optical element is located adjacent a portion of an outer periphery of distal portion of each optical fiber;
   inserting the device in a cavity;
   directing transmitted light through the device onto an inner wall of the cavity;
   collecting the light reflected back from the inner wall of the cavity; and
   utility the collected data to locate the vulnerable plaque.

21. The method according to claim 20, further comprising the step of utilizing interferometry or spectroscopy applications.

22. The method according to claim 20, wherein the plurality of optical fibers are non-rotating.

23. The method according to claim 20, wherein the device further comprises a transparent housing intermediate the outer periphery of the plurality of optical fibers and the optical element.

24. The method according to claim 20, wherein the device comprises a probe, guide wire or catheter.

25. The method according to claim 20, wherein the optical element is solid.

* * * * *